(12) United States Patent
Caleffi et al.

(10) Patent No.: US 8,728,020 B2
(45) Date of Patent: May 20, 2014

(54) INFUSION APPARATUS

(75) Inventors: Luca Caleffi, Carpi (IT); Ranko Sakota, Giugliano in Campania (IT); Giuseppe Franzoni, Sassuolo (IT)

(73) Assignee: Gambro Lundia AB, Lund (SE)

(*) Notice: Subject to any disclaimer, the term of this patent is extended or adjusted under 35 U.S.C. 154(b) by 263 days.

(21) Appl. No.: 12/681,487

(22) PCT Filed: Oct. 4, 2007

(86) PCT No.: PCT/IB2007/002949
§ 371 (c)(1),
(2), (4) Date: Jun. 16, 2010

(87) PCT Pub. No.: WO2009/044221
PCT Pub. Date: Apr. 9, 2009

(65) Prior Publication Data
US 2010/0280430 A1   Nov. 4, 2010

(51) Int. Cl.
*A61M 37/00* (2006.01)

(52) U.S. Cl.
USPC ......................................... 604/5.01

(58) Field of Classification Search
CPC ............... A61M 2001/14; A61M 2001/16; A61M 2001/1615; A61M 2001/34; A61M 2001/341
USPC .................................... 604/5.01, 8
See application file for complete search history.

(56) References Cited

U.S. PATENT DOCUMENTS

| | | | |
|---|---|---|---|
| 3,042,038 A * | 7/1962 | Beacham | 604/127 |
| 3,352,779 A * | 11/1967 | Austin et al. | 210/646 |
| 3,570,484 A | 3/1971 | Steer et al. | |
| 3,601,152 A | 8/1971 | Kenworthy | |
| 3,710,942 A | 1/1973 | Rosenberg | |
| 3,804,113 A | 4/1974 | Garcea | |
| 3,886,937 A | 6/1975 | Bobo et al. | |
| 3,889,710 A | 6/1975 | Brost | |
| 3,946,731 A * | 3/1976 | Lichtenstein | 604/66 |

(Continued)

FOREIGN PATENT DOCUMENTS

| | | |
|---|---|---|
| DE | 31 00 442 C1 | 9/1982 |
| DE | 39 22 291 C1 | 11/1990 |

(Continued)

OTHER PUBLICATIONS

Brochure GelmanSciences, "Supor Micro IV Air-Eliminating Filter", Section Liquid Filtration Devices, at least as early as Apr. 1, 2010, p. 31.

(Continued)

*Primary Examiner* — Susan Su
*Assistant Examiner* — Guy K Townsend
(74) *Attorney, Agent, or Firm* — Pearne & Gordon LLP

(57) ABSTRACT

In an infusion apparatus, an infusion line (4) connects a container (2) of an infusion fluid to an extracorporeal blood circuit (23). A first valve (6) closes the infusion line downstream of an infusion pump (5). An expansion chamber (9), provided with a pressure sensor (10), is arranged between the infusion pump and the first valve. A second valve (8) closes a vent line (7) of the expansion chamber. The processor closes the first valve when the container is emptied. After replacement with a new and full container, the processor restarts the pump and selectively opens the first valve or the second valve according to the increase in pressure measured in the expansion chamber.

32 Claims, 4 Drawing Sheets

(56) References Cited

U.S. PATENT DOCUMENTS

| | | | |
|---|---|---|---|
| 3,978,857 A | 9/1976 | McPhee | |
| 3,990,439 A | 11/1976 | Klinger | |
| 4,005,710 A | 2/1977 | Zeddies et al. | |
| 4,031,891 A | 6/1977 | Jess | |
| 4,044,983 A | 8/1977 | Francis | |
| 4,084,606 A | 4/1978 | Mittleman | |
| 4,086,924 A | 5/1978 | Latham, Jr. | |
| 4,141,379 A | 2/1979 | Manske | |
| 4,175,602 A | 11/1979 | Cavalaris et al. | |
| 4,181,146 A | 1/1980 | Goglio | |
| 4,187,057 A | 2/1980 | Xanthopoulos | |
| 4,190,426 A | 2/1980 | Ruschke | |
| 4,222,407 A | 9/1980 | Ruschke et al. | |
| 4,246,932 A | 1/1981 | Raines | |
| 4,286,628 A | 9/1981 | Paradis et al. | |
| 4,310,017 A | 1/1982 | Raines | |
| 4,349,035 A | 9/1982 | Thomas et al. | |
| 4,354,492 A | 10/1982 | McPhee | |
| 4,369,812 A | 1/1983 | Paradis et al. | |
| 4,370,983 A * | 2/1983 | Lichtenstein | 600/301 |
| 4,395,260 A | 7/1983 | Todd et al. | |
| 4,447,230 A | 5/1984 | Gula et al. | |
| 4,464,172 A * | 8/1984 | Lichtenstein | 604/65 |
| 4,515,535 A | 5/1985 | D'Silva | |
| 4,530,696 A | 7/1985 | Bisera et al. | |
| 4,535,820 A | 8/1985 | Raines | |
| 4,556,086 A | 12/1985 | Raines | |
| 4,605,503 A | 8/1986 | Bilstad et al. | |
| 4,618,343 A * | 10/1986 | Polaschegg | 604/29 |
| 4,629,448 A | 12/1986 | Carlsson et al. | |
| 4,646,781 A | 3/1987 | McIntyre et al. | |
| 4,683,916 A | 8/1987 | Raines | |
| 4,687,473 A | 8/1987 | Raines | |
| 4,711,715 A * | 12/1987 | Polaschegg | 210/103 |
| 4,729,401 A | 3/1988 | Raines | |
| 4,734,269 A * | 3/1988 | Clarke et al. | 96/156 |
| 4,819,684 A * | 4/1989 | Zaugg et al. | 137/112 |
| 4,832,689 A | 5/1989 | Mauerer et al. | |
| 4,874,359 A * | 10/1989 | White et al. | 604/6.09 |
| 5,025,829 A | 6/1991 | Edwards et al. | |
| 5,061,241 A * | 10/1991 | Stephens et al. | 604/114 |
| 5,064,168 A | 11/1991 | Raines et al. | |
| 5,112,298 A | 5/1992 | Prince et al. | |
| 5,147,313 A | 9/1992 | Dikeman | |
| 5,211,201 A | 5/1993 | Kamen et al. | |
| 5,308,333 A | 5/1994 | Skakoon | |
| 5,322,518 A | 6/1994 | Schneider et al. | |
| 5,349,852 A * | 9/1994 | Kamen et al. | 73/149 |
| 5,402,982 A | 4/1995 | Atkinson et al. | |
| 5,423,738 A * | 6/1995 | Robinson et al. | 604/6.01 |
| 5,439,451 A | 8/1995 | Collinson et al. | |
| 5,533,389 A * | 7/1996 | Kamen et al. | 73/149 |
| 5,575,310 A * | 11/1996 | Kamen et al. | 137/614.11 |
| 5,578,223 A * | 11/1996 | Bene et al. | 210/85 |
| 5,605,540 A | 2/1997 | Utterberg | |
| 5,613,663 A | 3/1997 | Schmidt et al. | |
| 5,616,124 A * | 4/1997 | Hague et al. | 604/65 |
| 5,617,897 A | 4/1997 | Myers | |
| 5,623,969 A | 4/1997 | Raines | |
| 5,634,905 A | 6/1997 | Rudolph, Jr. | |
| 5,651,893 A * | 7/1997 | Kenley et al. | 210/636 |
| 5,674,390 A * | 10/1997 | Matthews et al. | 210/261 |
| 5,698,090 A | 12/1997 | Bene et al. | |
| 5,705,066 A * | 1/1998 | Treu et al. | 210/233 |
| 5,714,060 A * | 2/1998 | Kenley et al. | 210/194 |
| 5,725,776 A | 3/1998 | Kenley et al. | |
| 5,727,594 A | 3/1998 | Choksi | |
| 5,762,782 A | 6/1998 | Kenley et al. | |
| 5,771,935 A | 6/1998 | Myers | |
| 5,810,770 A | 9/1998 | Chin et al. | |
| 5,863,421 A * | 1/1999 | Peter et al. | 210/134 |
| 6,032,926 A | 3/2000 | Fuchs | |
| 6,071,423 A | 6/2000 | Brown et al. | |
| 6,142,008 A | 11/2000 | Cole et al. | |
| 6,234,992 B1 | 5/2001 | Haight et al. | |
| 6,251,295 B1 | 6/2001 | Johnson | |
| 6,348,156 B1 | 2/2002 | Vishnoi et al. | |
| 6,350,249 B1 | 2/2002 | Zicherman | |
| 6,390,120 B1 * | 5/2002 | Guala | 137/512.15 |
| 6,390,130 B1 | 5/2002 | Guala | |
| 6,409,707 B1 | 6/2002 | Guala | |
| 6,537,258 B1 * | 3/2003 | Guala | 604/247 |
| 6,572,576 B2 * | 6/2003 | Brugger et al. | 604/4.01 |
| 6,616,633 B1 * | 9/2003 | Butterfield et al. | 604/151 |
| 6,638,478 B1 * | 10/2003 | Treu et al. | 422/44 |
| 6,808,369 B2 * | 10/2004 | Gray et al. | 417/38 |
| 7,037,428 B1 * | 5/2006 | Robinson et al. | 210/416.1 |
| 7,040,142 B2 * | 5/2006 | Burbank | 73/40 |
| 7,087,033 B2 * | 8/2006 | Brugger et al. | 604/4.01 |
| 7,141,037 B2 * | 11/2006 | Butterfield et al. | 604/67 |
| 7,316,662 B2 * | 1/2008 | Delnevo et al. | 604/6.16 |
| 2001/0045395 A1 | 11/2001 | Kitaevich et al. | |
| 2003/0009123 A1 * | 1/2003 | Brugger et al. | 604/4.01 |
| 2003/0100857 A1 * | 5/2003 | Pedrazzi et al. | 604/4.01 |
| 2004/0019313 A1 * | 1/2004 | Childers et al. | 604/5.01 |
| 2004/0069709 A1 * | 4/2004 | Brugger et al. | 210/646 |
| 2004/0243046 A1 * | 12/2004 | Brugger et al. | 604/4.01 |
| 2005/0045548 A1 * | 3/2005 | Brugger et al. | 210/252 |
| 2005/0119597 A1 * | 6/2005 | O'Mahony et al. | 604/4.01 |
| 2005/0131331 A1 * | 6/2005 | Kelly et al. | 604/4.01 |
| 2005/0131332 A1 * | 6/2005 | Kelly et al. | 604/4.01 |
| 2005/0209547 A1 * | 9/2005 | Burbank et al. | 604/5.01 |
| 2005/0209563 A1 * | 9/2005 | Hopping et al. | 604/151 |
| 2005/0247203 A1 * | 11/2005 | Chevallet et al. | 96/209 |
| 2005/0284815 A1 * | 12/2005 | Sparks et al. | 210/645 |
| 2006/0058774 A1 | 3/2006 | Delnevo et al. | |
| 2006/0195064 A1 * | 8/2006 | Plahey et al. | 604/151 |

FOREIGN PATENT DOCUMENTS

| | | |
|---|---|---|
| DE | 92 01 579.4 U1 | 4/1992 |
| DE | 100 23 600 C1 | 2/2002 |
| EP | 0 240 590 A1 | 10/1987 |
| EP | 0 247 213 A1 | 12/1987 |
| EP | 0 247 824 A2 | 12/1987 |
| EP | 0 261 317 A2 | 3/1988 |
| EP | 0 452 045 A1 | 10/1991 |
| EP | 0 474 069 A1 | 3/1992 |
| EP | 0 477 973 A1 | 4/1992 |
| EP | 0 638 328 A1 | 2/1995 |
| EP | 0 704 224 A2 | 4/1996 |
| EP | 0 790 065 A2 | 8/1997 |
| EP | 0 848 964 A1 | 6/1998 |
| EP | 1 099 456 A1 | 5/2001 |
| EP | 1 099 457 A2 | 5/2001 |
| EP | 1 319 417 A1 | 6/2003 |
| FR | 2 734 726 A1 | 12/1996 |
| GB | 2 000 685 A | 1/1979 |
| WO | 87/05225 A1 | 9/1987 |
| WO | 97/02056 A1 | 1/1997 |
| WO | 01/89599 A2 | 11/2001 |
| WO | 02/03878 A1 | 1/2002 |
| WO | 2004/004807 A1 | 1/2004 |

OTHER PUBLICATIONS

Brochure GelmanSciences, "Supor Pediatric IV Air-Eliminating Filter", Section Liquid Filtration Devices, at least as early as Apr. 1, 2010, p. 30.

Brochure GelmanSciences, "Syringe Volume Filters", Section Liquid Filtration Devices, at least as early as Apr. 1, 2010, p. 32.

Brochure PALL Medical, "Supor IV-3 Air-Eliminating Filter", at least as early as Apr. 1, 2010, p. 29.

* cited by examiner

INFUSION APPARATUS

BACKGROUND OF THE INVENTION

The invention relates to an infusion apparatus and to a control method for an infusion apparatus.

Specifically, though not exclusively, the invention can be usefully applied for infusion of a medical fluid to a patient, either directly into the patient's body, for example into his or her vascular system, or via an extracorporeal blood circuit connected to the patient.

WO 87/05225 teaches an infusion system comprising a drip chamber having a pointed upper inlet end for insertion of a container of an infusion fluid. The chamber is provided with an inlet valve and an outlet valve controlled by a control unit. The top of the chamber is connected to a piston gas compressor via an auxiliary line provided with a pressure sensor. The control of the infusion flow rate is done as follows. With both the valves closed and an initial pressure $P_1$ in the chamber, the piston is displaced forward such as to reduce the volume by a predetermined quantity $\Delta V$. According to Boyle's law, this reduction in volume corresponds to a proportional increase in gas pressure $\Delta P$. At this point the outlet valve is opened to dispense the infusion fluid. When the pressure has dropped by a quantity $\Delta P$, which means that an infusion fluid volume of $\Delta V$ has been dispensed, the outlet valve is closed. After this the piston returns back to its initial position, the inlet valve is opened so the chamber can be filled to initial pressure $P_1$, and a new cycle commences.

EP 1319417 illustrates a disposable infusion system for injecting an infusion fluid into the body of a patient. The infusion system comprises a fluid conduit situated between a source of an infusion fluid and the patient, a peristaltic pump operating on the fluid conduit, a gas-liquid separation chamber downstream of the pump, a pressure sensor in the chamber, and a clamp for blocking the fluid conduit downstream of the chamber. The pressure sensor is arranged on a service line which branches from the top of the chamber and which is provided with a hydrophobic-membrane protection device for protecting the pressure sensor against contamination by the liquid in the chamber. If the liquid reaches the membrane the membrane becomes gas-sealed and is no longer able to transmit the pressure to the sensor. In these conditions the measured pressure does not correspond to the real pressure in the chamber. A monitoring unit determines the quantity of gas in the system so as to detect, over time, a situation of risk of the liquid reaching the membrane. The monitoring unit measures the initial pressure $P_1$, and then injects into or extracts from the system a predetermined fluid volume $\Delta V$, after which it newly measures the pressure $P_2$, and calculates the gas volume in the system as a function of $P_2$, $P_1$ and $\Delta V$.

EP 1319417 teaches a further monitoring method of a disposable fluid conduit system connected to a medical apparatus, in particular with the aim of testing the integrity of the system (for example the absence of leaks) and of checking that the installed disposable system is the appropriate one for the desired treatment. The monitoring method includes continuously measuring the pressure in the system, injecting or extracting a volume of fluid $\Delta V$ into or from the system until a predetermined pressure $P_2$ is reached in the system, and finally determining the state of the system from a comparison between $\Delta V$ and a standard predetermined value.

SUMMARY OF THE INVENTION

An aim of the present invention is to provide a fluid infusion liquid in which the risk of infusion of gaseous parts (air) present in the liquid itself is reduced.

A further aim of the invention is to realise a control method for reducing the above-mentioned risk.

An advantage of the invention is to provide an infusion apparatus which can reduce the need for intervention on the part of an operator, with the aim of reducing the risk of the presence of gaseous parts (air) in the infusion liquid. In particular the invention enables a reduction or elimination of the interventions required by the operator in order to eliminate excesses of air in the infusion circuit.

A further advantage is automatically to eliminate excess air in the infusion circuit, in particular each time a used container of the infusion fluid is replaced with a new and full container. The excess air can advantageously be eliminated during a first infusion circuit priming stage, or in a first filling stage of the infusion circuit with a liquid which expels air from the circuit at the same time.

A further advantage is to make available an infusion apparatus which is constructionally simple and economical and which is also very reliable.

These aims and others besides are all attained by the invention as it is characterised in one or more of the accompanying claims.

In a specific embodiment of the invention, the infusion apparatus may comprise a batch container of an infusion fluid, an infusion line connected to the batch container, an infusion pump operating on the infusion line, an infusion block valve arranged downstream of the infusion pump, and a vent valve arranged between the infusion pump and the block valve. In a specific embodiment of the invention, the infusion apparatus may comprise a gas-liquid separator (for example a separation or expansion chamber) arranged between the infusion pump and the block valve, and a sensor designed to provide a signal indicating the quantity of liquid and/or gas in the gas-liquid separator. The sensor may comprise, for example, a pressure sensor for providing a signal of the liquid level in the separator, or a float device for providing a signal when a predetermined liquid has reached a predetermined level in the separator, and so on.

In a specific embodiment of the invention, the infusion apparatus may comprise an infusion line, a pump operating on the infusion line, an infusion block valve arranged downstream of the pump, a vent valve arranged between the pump and the block valve, a pressure sensor arranged between the pump and the block valve, and a processor programmed to perform the operations of: closing both the valves in at least a particular situation, for example when the infusion fluid container is to be changed; activating the pump with both valves closed; and selectively re-opening one or the other of the valves according to the pressure signal provided by the pressure sensor.

In a specific embodiment of the invention, the processor may be programmed to selectively re-open one or the other valve according to a value indicating the ratio between the pressure change measured by the pressure sensor and the volume of fluid pumped by the pump during the above-cited measured pressure change.

In a specific embodiment of the invention, the processor may be programmed to stop the pump when the pressure measured by the pressure sensor exceeds or reaches a predetermined threshold level.

Further characteristics and advantages of the present invention will better emerge from the detailed description that follows of some embodiments of the invention, illustrated by way of non-limiting example in the accompanying figures of the drawings.

BRIEF DESCRIPTION OF THE DRAWINGS

The description will be made herein below with reference to the accompanying figures of the drawings, which are provided by way of non-limiting example.

DETAILED DESCRIPTION

Figure 1:
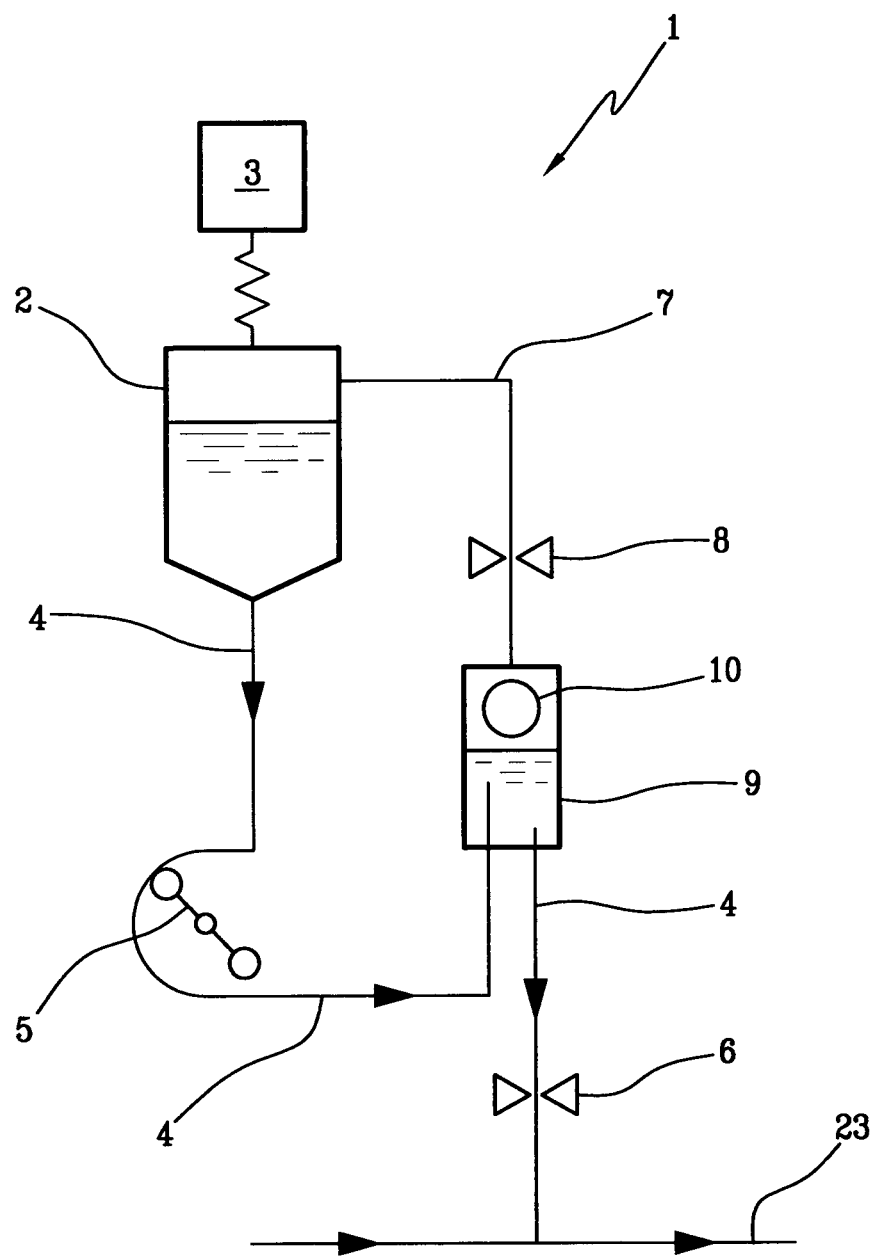
FIG. 1 illustrates a first embodiment of the infusion apparatus made according to the invention.

With reference to FIG. 1, 1 denotes in its entirety an infusion apparatus for infusing a fluid, in particular a medical fluid, into a human being. The infusion apparatus 1 can be used for infusing a medical fluid into the vascular system of a patient. This infusion can occur directly, i.e. by means of a direct connection with a vascular access device, or by means of an extracorporeal blood circuit 23, such as for example a usual blood circuit of a dialysis set. The infusion fluid (medical fluid) can comprise a replacement fluid used in a hemo (dia)filtration treatment. In particular it can comprise a replacement fluid used in an AFB treatment ("acetate free biofiltration"). The medical fluid can however comprise any known type of infusion fluid which can be introduced into a human body.

The infusion apparatus 1 comprises a container 2 having a limited capacity and containing the infusion fluid. The container 2 is a batch container. In other words the container 2 may be configured for discrete and not continuous functioning, i.e. it may be filled before use with a determined quantity of infusion fluid and be emptied during use while supplying the infusion fluid to a user. In substance the infusion system described herein may refer to infusion of a medical fluid in which the medical fluid is sourced from a batch-type source, i.e. a supply system in which the infusion fluid is prepared in one or more batches in discrete quantities which, during use, empty and which can be replaced time-by-time as they are emptied.

The container 2 can comprise one or more bags having flexible walls. The container 2, of known type, is provided with one or more access ports each provided with a sealing device of known type, for example a breakable membrane and/or a removable cap, or another type.

The batch container 2 of the infusion fluid is connected to a weight sensor 3 designed to emit a weight signal in relation to the weight of the container. The weight sensor 3 can comprise any type of scales of known type.

The infusion apparatus 1 further comprises an infusion line 4 having a first end which is connected to the container 2 in order to receive the infusion fluid, and a second end for supplying the infusion fluid to the user (for example the extracorporeal blood circuit 23). The infusion line 4 can comprise any type of infusion line of known type. The first end of the line 4 is connected to the container 2 by means of a known-type connection, for example by means of a removable connection (as illustrated and denoted by 13 in FIGS. 3 and 4), such as in particular a luer connector, or a piercing nozzle-type connection (the nozzle being associated to the first end of the line 4) which penetrates into a perforable or breakable closure predisposed on the access port of the container 2. It is however possible to use any type of known connection between an infusion line and an infusion fluid container. A removable-type connector enables simple and rapid changing of the container 2 when empty for a new and full container 2, while maintaining the operativity of the other elements of the infusion apparatus.

The infusion apparatus 1 further comprises an infusion pump 5 operating on the infusion line 4 for circulating the infusion fluid from the first end to the second end of the line itself. The infusion pump 5 may be an occlusive-type pump, i.e. a pump which in a non-activated condition, or when stationary, occludes the infusion line 4. The infusion pump 5 may be a positive-displacement pump. The infusion pump 5 can comprise, for example, a tube-deforming pump (peristaltic). In the specific embodiment the pump is rotary. The infusion line 4 comprises a pump tract designed for coupling with the infusion pump 5. In the specific embodiment the pump tract comprises a segment of tube which is open-ring-shaped (for example a U shape) which engages with a roller rotor belonging to the rotary peristaltic pump. It is, however, possible to use other known types of pumps (in particular positive displacement pumps) for circulating the fluid in a fluid transport line, in particular of the types used in medical lines.

The infusion apparatus 1 comprises a first valve 6, or a check valve of the infusion fluid, designed to close the infusion line 4 between the infusion pump 5 and the second end of the infusion fluid supply line. The first valve 6 comprises, in the specific case, a valve commanded by the control unit of the infusion apparatus 1. A manual valve, operated by the operator, could be used. The first valve 6 can comprise a mobile obturator organ which operates by squeezing a tract of tube of the infusion line 4. This tract of tube has elastic return properties, such as to return into the open configuration allowing fluid passage on reopening of the valve. The first valve 6 comprises, in the embodiment, a tube-blocking clamp of known type, e.g. electromagnetically activated.

The infusion apparatus 1 further comprises a vent line 7 having a first end which is connected to an intermediate tract of the infusion line 4 and a second discharge end. This intermediate tract of the infusion line 4 is arranged between the infusion pump 5 and the first valve 6. The vent line 7 comprises, in the specific case, a length of flexible tube used for fluid transport in the medical area. The vent line 7 serves, in particular, to expel excess gas from the intermediate tract of the infusion line 4, as will be better explained herein below.

The vent line 7 is provided with a second valve 8, or a vent valve in the intermediate tract of the infusion line, designed to close the line 7 itself. The second valve 8 comprises, in the specific case, a valve commanded by the control unit of the infusion apparatus. A manual valve activated by the operator could also be used. The second valve 8 can comprise a mobile obturator which operates by squeezing a tract of tube of the vent line 7. The tract of tube has elastic return properties, so as to return into the open configuration, allowing fluid passage, on reopening the valve. The second valve 8 comprises, in the example, a tube blocking clamp of known type, e.g. electromagnetically activated.

The infusion apparatus 1 comprises an expansion chamber 9 arranged in the intermediate tract of the infusion line. The expansion chamber 9 is in effect an enlargement of the fluid passage section of the infusion line 4. The expansion chamber 9 produces a slowing down of the infusion fluid flow along the infusion line 4. The expansion chamber 9 may have a transversal section having a greater surface than the transversal section of the two tracts of tube which are part of the infusion line 4 and which are constituted by an inlet tract of the chamber 9 (on which the pump 5 operates) and by an ouelet tract from the chamber 9 (on which the first valve 6 operates). The tract of inlet infusion line in the expansion chamber may be connected to the container 2 of the infusion fluid, while the tract of outlet infusion line from the expansion chamber is connected to the user (blood circuit). The infusion line 4 may exhibit an inlet into the expansion chamber 9 and an outlet from the expansion chamber 9, in which the inlet is located at a higher position than the outlet. The expansion chamber 9 functions as a gas/liquid separator. The expansion chamber 9 may be destined to contain a determined quantity of infusion fluid such as to maintain a liquid level delimiting an upper part of the chamber which is full of air.

The infusion apparatus 1 can further comprise a first pressure sensor 10 for emitting a first signal indicating the pressure in the above-mentioned intermediate tract of infusion line 4. In the specific case the first pressure sensor 10 is operatively associated to the expansion chamber 9. In particular the first pressure sensor 10 may be an elastically-deformable membrane sensor having an internal side which faces towards the inside of the expansion chamber 9 and an external side which communicates with a pressure transducer (of known type and not illustrated) connected to the control unit of the infusion apparatus 1. The pressure transducer may be predisposed such as to be able to measure the pressure in the inside of the expansion chamber 9. The first elastically-deformable membrane sensor 10 may be solidly associated to the body of the expansion chamber 9. In particular, the membrane can have the edge thereof tightly engaged between two half-shells which are part of the body of the expansion chamber 9. It is possible to use other types of known pressure sensors, such as for example the pressure sensors already used in the medical field for measuring the pressure in extracorporeal blood circuits. In particular it is possible to use a pressure sensor comprising a service line connecting the expansion chamber 9 with a pressure transducer—in turn connected to the control unit of the infusion apparatus—via the interpositioning of a transducer-protector device having a hydrophobic membrane (also known as a blood catcher).

In the specific example the first end of the vent line 7 is connected with an access port arranged at the top of the expansion chamber 9. The vent line 7 may open into the upper part of the expansion chamber 9 which, in use, may be occupied by a volume of gas (air) which overlies the liquid level in the lower part. The second end of the vent line 7 may be connected, as in the specific example, with the part of the infusion line 4 located upstream of infusion pump 5, so as to form a ring. In particular the vent line 7 may have the second end engaged (fixed or removably) in an access port arranged on the infusion fluid container wall 2. In other embodiments the second end of the vent line can be connected to an element chosen from a group of elements comprising, apart from the container 2 of the infusion fluid: an initial tract of the infusion line 4 comprised between the container 2 and the pump 5, a hydrophobic filter connected to the atmosphere, an aspirating device, a fluid transport line connected to a fluid chamber of a blood treatment device having a semipermeable membrane which separates the fluid chamber from a blood chamber, and a used fluid discharge line of a hemo(dia)filtration apparatus. In figures from 2 to 4, some examples of these different embodiments are illustrated.

The control unit (processor) of the infusion apparatus 1 is connected to the first pressure sensor 10 in order to receive the pressure signal of the internal pressure in the expansion chamber 9. The control unit may be further connected to the weight sensor 3 in order to receive the weight signal of the container 2 of the infusion fluid. The control unit may be designed to control the infusion pump 5, the first valve 6 (infusion fluid check valve) and the second valve 8 (vent valve of the intermediate tract of the infusion line 4).

During the normal process of infusion the control unit controls the infusion pump 5 according to the weight signal received from the weight sensor 3, with the aim of providing a predetermined flow rate of the infusion pump 5 in order to obtain the desired dose of infusion fluid. During the normal infusion process the control unit maintains the first valve 6 open and the second valve 8 closed. The control unit further monitors the pressure in the expansion chamber 9 in order to detect any faults in the infusion process—faults which are recognised if, for example, the pressure in the expansion chamber 9 no longer falls within one or more predetermined safety ranges—and in order to intervene automatically such as to place the infusion apparatus in safety conditions vis-à-vis the patient. The faults which might occur are, for example, possibly a blockage or obstruction in the infusion line 4, of a leakage of liquid in the line itself, or a malfunctioning of the infusion pump 5, and others besides.

The control unit of the infusion apparatus may be programmed to automatically perform a procedure of recognition that the container 2 of the infusion fluid has emptied, and a procedure for restarting the infusion process after replacement of the empty container 2 with a full one.

As mentioned herein above, the control unit is programmed to perform the normal infusion procedure, in which the first valve 6 is opened and kept open in order to allow the infusion fluid to flow towards the user (blood circuit), while the infusion pump 5 is activated with the first valve 6 open in order to supply the desired flow rate under the control according to the weight signal supplied by the weight sensor 3. In substance, the control unit acquires at least a weight value for the container 3 (for example it can acquire a series of values according to one or more predetermined measuring frequencies), compares the weight value detected against a reference value, and on the basis of this comparison controls the infusion pump flow rate. The reference value can be, for example, the value of the weight measured in the preceding step, or a series of weight values measured during the previous steps. The control of the normal infusion weight is however substantially of known type and can be performed in any of the systems in the prior art (for example by a usual PID retroactive control). The recognition procedure for detecting an empty infusion fluid container is also substantially of known type and can comprise any one of the known systems for recognising the emptying of a container (end bag). This procedure can comprise, for example, a stage of comparing a weight value detected (for example, the last one) with a reference value which can be constituted, for example, by a previously-acquired weight value of the container (for example the penultimate one) with the aim of assessing whether the weight of the container is no longer dropping. In substance the control unit may note that the container 2 is empty because its weight no longer drops over a certain period of time. Another system can compare against a reference value constituted by a predefined value indicating the weight of the container 2 when empty of fluid. In this case the weight of the container can be known before. If the control unit recognises that the container 2 is empty, it intervenes to put the system into safety mode; this intervention can comprise, for example, one or more of the following actions: signalling a faulty situation (for example by emitting a sound or a visual signal via the user interface connected to the control unit) and/or stopping the infusion pump 5 and/or closing the first valve 6. These procedures, as is known, have the drawback of almost inevitably causing ingress of air into the infusion line 4. This air can be separated in the expansion chamber 9, giving rise however to a lowering of the liquid level in the chamber itself. If the level gets too low there is the risk that, on restarting the infusion process after having replaced the empty container 2 with a new full container 2, there might be air which can be directed towards the zone of use (blood circuit), with grave risks to the health of the patient.

To obviate this drawback, the control unit of the infusion apparatus may be programmed to perform the following control procedure of the infusion on restarting the infusion process, after changing the empty container 2 with a full container 2 of the infusion fluid. This control procedure can be activated by the operator who, after having replaced the container 2, gives the control unit the instruction or series of instructions for initiating the control procedure. This instruction can comprise, for example, a command (such as a button or a touch-button of a touch-screen) given on the user interface of the infusion apparatus. The control procedure may comprise a stage of acquiring the pressure signal in the expansion chamber 9 (i.e. in the intermediate tract of the infusino line 4 comprised between the infusion pump 5 and the first valve 6) and a stage of selectively commanding the opening of either the first valve 6 or the second valve 8 on the basis of the pressure value measured. In particular acquiring the pressure value (or series of pressure values) in the expansion chamber 9 may be done after having activated the infusion pump 5. This activating of the pump 5 will produce a flow in the direction going from the infusion container 2 to the expansion chamber 9. Since both the first valve 6 and the second valve 8 are closed, in this configuration the intermediate tract of the infusion line 4—which comprises the expansion chamber 9—forms a closed system. Thus the flow of a certain quantity of fluid into the intermediate tract will determine a certain pressure increase, which can be measured by the pressure sensor 10. If this pressure increase is relatively high, it means that the fluid which has entered the intermediate tract moved by the positive-displacement pump 5 contains a relatively high percentage of liquid part with respect to gaseous part. If, on the other hand, this pressure increase is relatively small, it means that the fluid moved into the intermediate tract of the pump 5 contains a relatively high percentage of gas with respect to liquid. In other words, the pressure change in the intermediate tract, assessed in relation to the volume of fluid which the positive-displacement pump 5 pushes into the intermediate tract, provides an indicator of the quantity of gas (air) introduced into the intermediate tract. The control unit may be therefore programmed to stop the pump 5 when the pressure in the intermediate tract exceeds a predetermined threshold level. This threshold level can be, for example, predetermined according to the desirable working pressure required in the expansion chamber 9 during the normal infusion process. This working pressure is correlated in a known way to the volume of the expansion chamber 9, to the level of liquid in the chamber 9 and to the desired quantity of air required in the chamber during the normal infusion process. The quantity of air in the chamber will depend on the working pressure and the desired level of liquid, once the volume of the expansion chamber 9 is fixed and known (which is in the present example is not variable). Let us suppose that the above-cited threshold value is made to coincide with the working pressure value or with a value close thereto. In this case, the control unit may be programmed to stop the pump 5 on reaching the cited pressure and to decide, at this point, whether to open the second valve 8 (vent valve) or the first valve 6 (infusion blocking valve) on the basis of a criterion depending on the volume pumped by the pump 5 in the intermediate tract in order to reach the predefined pressure. In particular, the second valve 8 may be opened if the pumped volume is relatively high (for example above a prefixed threshold value), because this means, as previously mentioned, that in the volume of fluid pumped (which has entered the intermediate tract) there is a high quantity of gas with respect to the liquid. The opening of the second valve 8 will thus produce removal of part of the air contained in the intermediate tract. The second end of the vent line 7 (i.e. the end beyond the vent valve 8) is in communication with an environment kept at a pressure which is below the pressure reached in the expansion chamber 9. In other words, the opening of the vent valve 8 will produce a reduction in the pressure in the expansion chamber 9 (intermediate tract of the infusion line) such as to reach a situation of equilibrium with the environment in which the vent line 7 terminates. At this point the vent valve (second valve 8) is closed and a new cycle of activating the infusion pump 5 may begin, up until it newly reaches the threshold pressure in the intermediate tract. As long as the pumped volume in each pumping cycle is relatively high, the cycle (i.e. in which the control unit opens the second valve 8—vent valve—to enable expulsion of the excess air and thus the lowering of the pressure) is repeated. If on the other hand the pumped volume is relatively small (for example less than a predetermined threshold value), the first valve 6 may be opened (infusion blocking valve) and the normal infusion process can recommence, as this means, as previously mentioned, that there is a small or almost negligible amount of gas in the volume of pumped fluid (which has entered the intermediate tract). In the latter case, in substance, it is taken that there is no longer any air internally of the infusion line 4 upstream of the chamber itself and that the liquid level in the chamber 9 is the desired level; thus the normal infusion process can be restarted without any danger of an undesired ingress of air and without the liquid level in the chamber lowering any further.

The control unit for the infusion apparatus, as has been described, may be therefore programmed to close the first valve 6 and the second valve 8, to activate the pump 5 and to command a selective opening of the first valve 6 or the second valve 8 on the basis of the pressure signal received. In particular, the control unit may compare the pressure value received with a reference value (predefined and stored in the control unit's memory), and open the second valve 8 following the comparison. During the pump 5 activation stage, the control unit may be programmed to close the first valve 6 and to leave it closed at least during the above-described pump 5 activation stage 5, so that the intermediate tract of the infusion line (where the expansion chamber 9 is located) forms a closed system.

The control unit may be programmed to perform a sequence of stages which comprises: closing the first valve 6 and the second valve 8, activating the pump 5, determining at least a value of pressure change in the intermediate tract during a predetermined variation of another parameter while the pump 5 is in the activation stage, comparing the above-mentioned pressure variation value with a reference value, and opening the first valve 6 or the second valve 8 according to the comparison. During this sequence of stages the first valve 6 and the second valve 8 may be both closed. The above-mentioned other parameter is, in the specific case, the volume of fluid pumped by the infusion pump 5, or a parameter indicating this volume (such as for example the number of revolutions of the rotary positive displacement infusion pump). The above-mentioned other parameter can be selected from the group of parameters comprising, apart from the volume of pumped fluid, the time, the displacement of a mobile element of the infusion pump 5, the weight of the container 2 of the infusion fluid.

The control unit may be programmed to perform the following sequence of stages: closing the first valve 6, closing the second valve 8, activating the pump 5 with the first valve 6 closed and the second valve 8 closed, acquiring at least a pressure value in the intermediate tract (for example while the pump 5 is in the stage of activation or after it has been functioning for a certain period of time), acquiring at least a value of the pressure change in the intermediate tract (for example while the pump 5 is in the stage of activation or after it has been functioning for a certain period of time), opening the second valve 8 when the pressure value exceeds a threshold value, re-closing the second valve 8 and repeating the above-mentioned stages up until the pressure change value has reached a threshold value. In substance, the pumping cycle may be interrupted and then recommences with the normal infusion process (opening the first valve 6) when the derivative of the pressure as a function of another parameter (where by derivative we mean the pressure change measured on varying the other parameter, which can be, for example, the time or fluid volume pumped or the weight of the fluid pumped) is sufficiently high.

Figure 2:
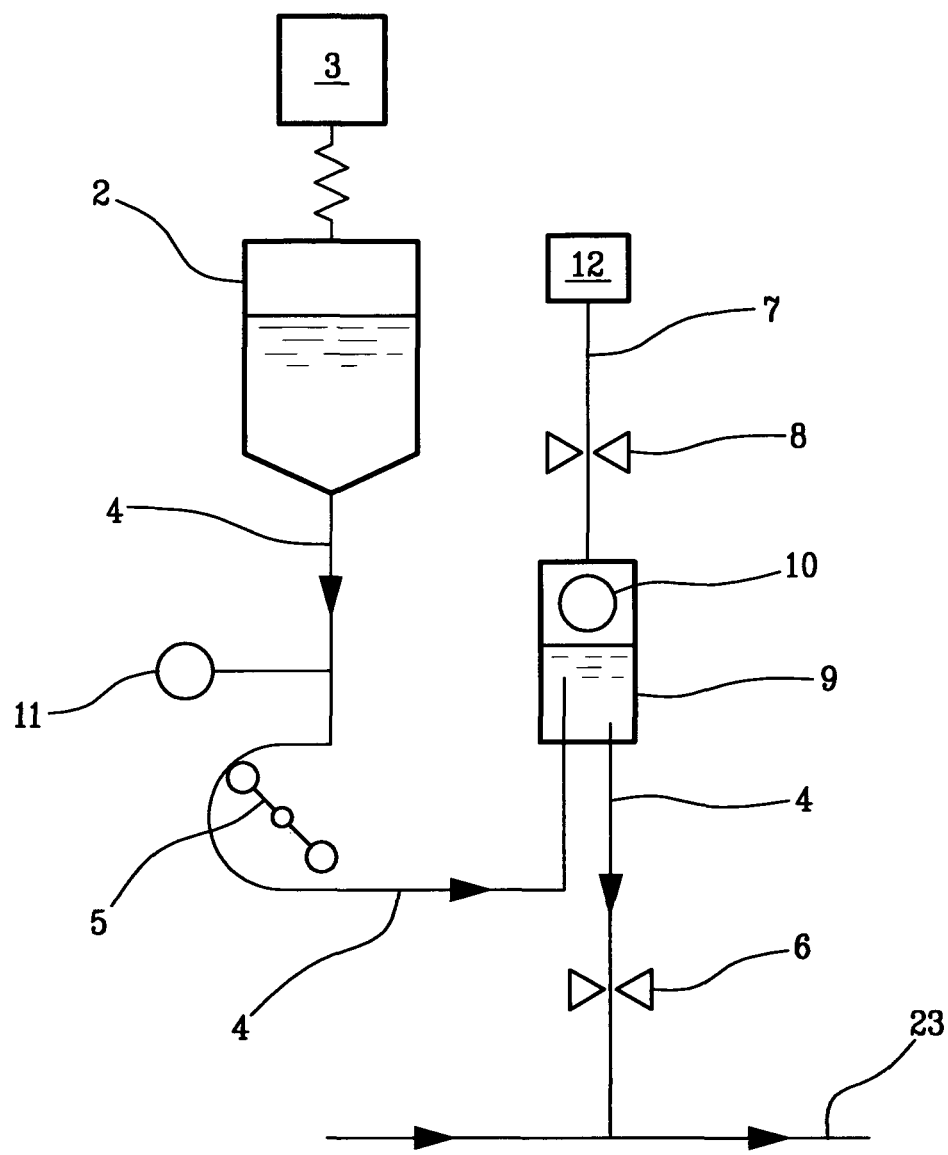
FIG. 2 is a second infusion apparatus made according to the invention.

In a further embodiment (see FIG. 2, in which the same elements as those in FIG. 1 have been denoted using the same numbers) the infusion apparatus further comprises a second pressure sensor 11 for emitting a second signal indicating the pressure in an initial tract of infusion line 4 comprised between the container 2 and the pump 5. The second pressure sensor 11 can comprise any known pressure sensor used in a fluid circuit for medical use. In the case of FIG. 2 the control unit may be programmed to perform the following sequence of stages: acquiring at least a pressure value in the initial tract supplied by the second pressure sensor 11, comparing the above-cited pressure value in the initial tract with a reference value, and signalling a faulty situation and/or stopping the pump 5 and/or closing the first valve 6 according to the result of the comparison. A reduction of pressure to below a theshold value and/or a rapidity in the reduction of pressure going beyond a certain threshold are seen as indicating the fact that the container has been emptied of infusion fluid and that therefore the outflow from the container essentially contains air. This may serve to stop the infusion pump in order to interrupt and prevent the flow of air towards the expansion chamber 9. In substance, the second pressure sensor 11 may be used to reduce the risk of undesired ingress of air into the intermediate tract of infusion line 4 arranged downstream of the pump 5, i.e. to prevent inflow of air into the expansion chamber 9 and thus the lowering of the liquid level in the chamber itself. In FIG. 2, the number 12 schematically denotes the environment into which the excess gas (air) is discharged into the expansion chamber 9 through the second vent valve 8. The environment can comprise one of those already mentioned herein above. An embodiment can be realised in which the weight sensor 3 is not present. In this case the function of signalling the emptying of the batch container 2 can be performed by the pressure sensor (as seen herein above).

Figure 3:
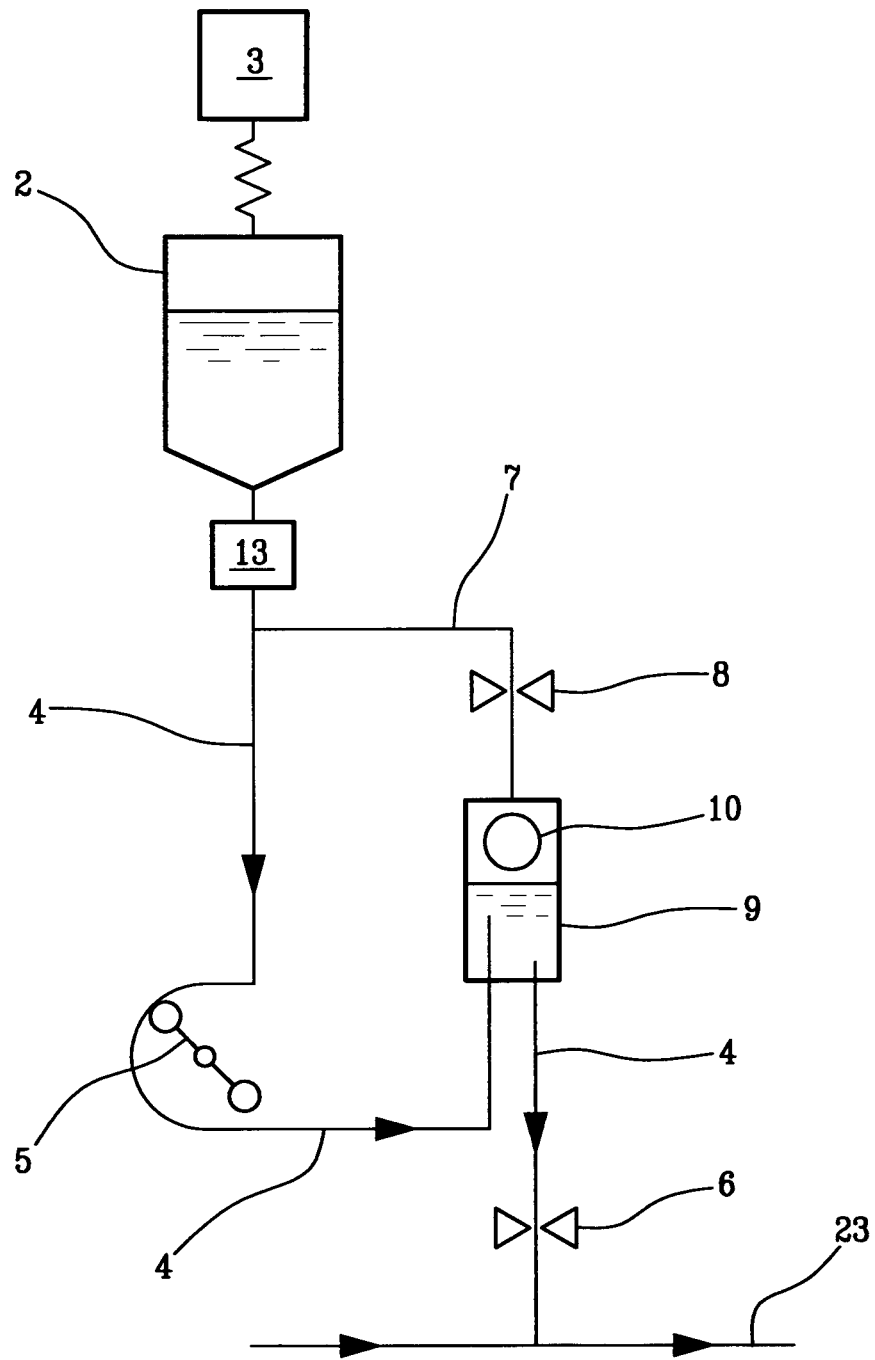
FIG. 3 is a third infusion apparatus made according to the invention.

A further embodiment is illustrated in FIG. 3, where the same elements as in FIGS. 1 and 2 have been denoted using the same numbers. The vent line 7 may be joined, at the second end in order to discharge the excess gas, to an initial tract of the infusion line 4 comprised between the container 2 outlet and the infusion pump 5. The second end of the vent line 7 may be, as in the specific case, connected to the infusion line 4 at an engagement point arranged between a removable connection 13 and the infusion pump 5. The engagement between the vent line 7 and the infusion line 4 can be either fixed and/or permanent, as in the specific embodiment, or can be removable. The removable connection 13 may be predisposed to connect an end of the infusion line 4 with the container outlet 2. The container outlet 2 may be arranged on the bottom of the container, with reference to a use configuration. The removable connection 13 can be a luer-type connection, or any other removable connection of known type.

Figure 4:
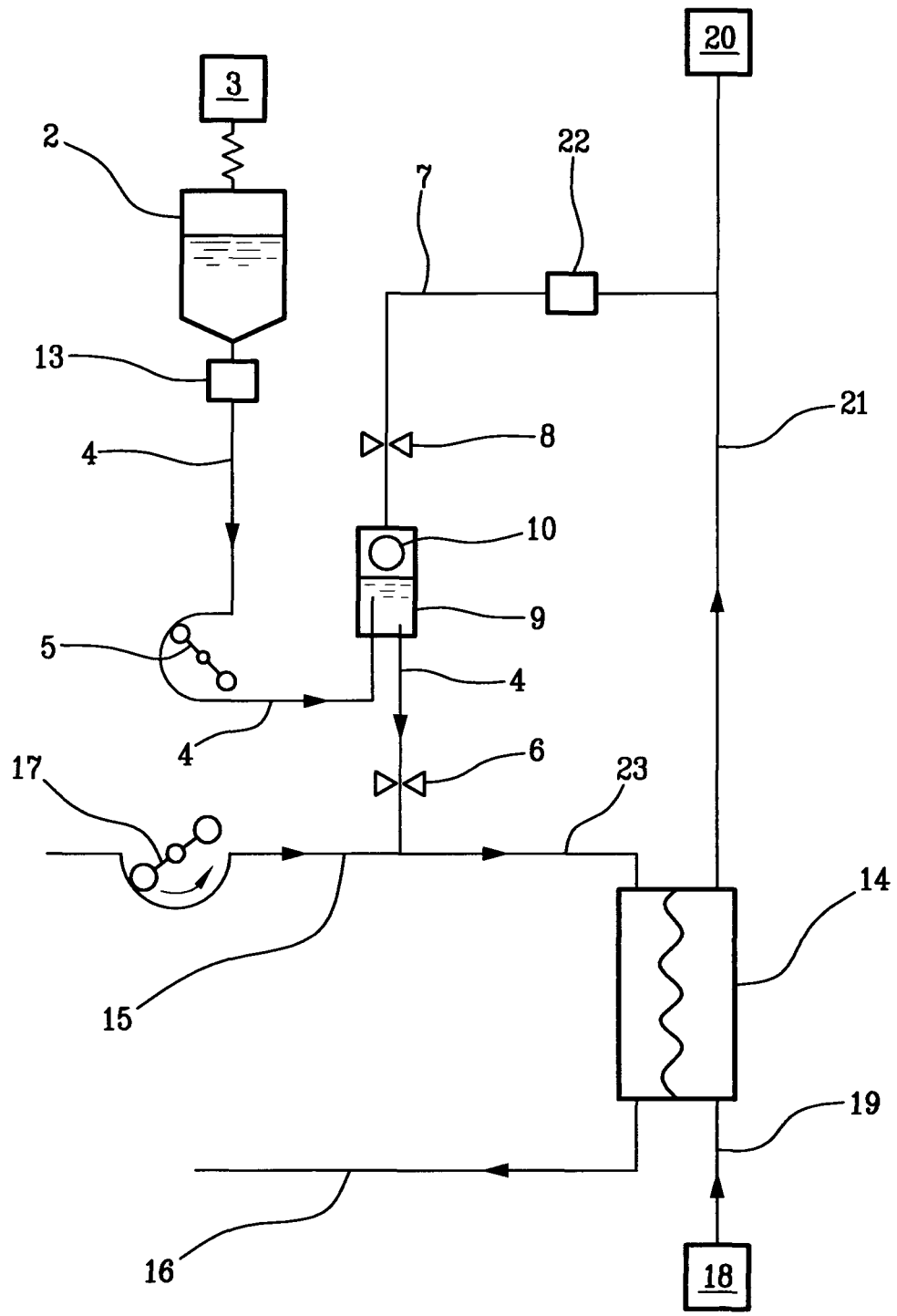
FIG. 4 is a fourth infusion apparatus made according to the invention.

A further embodiment is illustrated in FIG. 4, where the same elements as in FIGS. 1, 2 and 3 are denoted using the same numbers. The vent line 7 may be joined, at the second end for discharge of the excess gas, to a fluid transport line which is part of an apparatus for extracorporeal blood treatment. In the specific case of FIG. 4, the apparatus comprises a membrane device 14 for extracorporeal blood treatment. The membrane device 14 comprises, for example, a hemodialyser, or a hemo(dia)filter, or another type of membrane exchanger of known type for performing a hemoperfusion treatment, or a pure ultrafiltration, or a therapeutic plasma exchange, or a congestive heart failure treatment, or hepatic function substitution, and so on. The blood chamber of the membrane device 14 may be connected to an extracorporeal blood circuit having a withdrawal or removal line 15 for removing blood to be treated sourcing from a vascular access of the patient, a return line 16 for returning the treated blood the vascular system of the patient, a blood pump 17 for moving the blood along the extracorporeal circuit. The withdrawal line 15 and the return line 16 are connected respectively to an inlet and an outlet of the blood chamber of the membrane device 14. The fluid chamber of the membrane device 14 is connected to a hydraulic circuit which may comprise a source 18 of a fresh treatment fluid (for example an on-line preparation devcice of a dialysis fluid, or any other known type of a dialysis fluid source or a replacement fluid of a convective replacement therapy of the renal function, or any other known type of source of a medical fluid for replacement therapy of the hepatic function), a supply line 19 of the fresh treatment fluid which connects the source 18 with an inlet of the fluid chamber of the membrane device 14, a drainage 20, and a discharge line 21 of the used treatment fluid which connects and outlet of the fluid chamber of the membrane treatment device 14 with the drainage 20. The extracorporeal treatment apparatus is illustrated schematically in FIG. 4: it can however be constituted by any apparatus for hemodialysis or hemo(dia)filtration of known type. In the specific example the second end of the vent line 7 is connected to the discharge line 21, for example by means of a fluid-sealed removable connection 22 (a luer connection or another type of removable connection of known type).

A further embodiment could be realised, comprising a similar apparatus to that of FIG. 4, provided with an infusion device which is configured for providing an infusion line in post-dilution (downstream of the membrane device 14), the pre-dilution line being predisposed in addition to or alternatively to the predilution line of FIG. 4.

The functioning of the infusion systems illustrated in figures from 2 to 4 is the same as that of FIG. 1.

The process for obtaining the desired liquid level as described above can be applied not only to the case of a change of batch container of the infusion fluid, but also during the infusion circuit priming procedure, i.e. during a first filling stage of the infusion circuit with a liquid which contemporaneously expels the air from the circuit.

The method for controlling the infusion apparatus as described above, as has been seen, can be based on the analysis of the pressure (or another signal indicating the quantity of liquid and/or air, such as for example a liquid level signal) in the tract of the infusion line arranged downstream of the infusion pump (positive displacement and occlusive). The control method can comprise, as mentioned, an initial stage of closing the first valve (the block or check valve of the infusion flow to the user) when the container has been emptied. The detection of the emptying of the container is performed, for example, by means of monitoring the weight of the container and/or the pressure upstream of the infusion pump. After the first valve has been closed the empty container is replaced with a full container; this operation can activate, for example with a command (pressing a button) on the user interface of the infusion apparatus, the automatic procedure for evacuating any air from the infusion line before resetting the normal infusion flow to the user. The automatic procedure can be performed in various ways. In a first way, the pump may be activated (with the two valves, the vent valve and the block valve both closed) up until a predetermined pressure (or liquid level) is reached downstream of the pump; if the volume of fluid pumped by the pump to reach the pressure (or liquid level) is above a threshold value, the vent arranged downstream of the pump may be opened in order to evacuate the excess air and thus lower the pressure downstream of the pump, after which the vent may be closed and the operative cycle repeated, so that the pump is activated up until it newly reaches the above-mentioned predetermined pressure (or liquid level) downstream of the pump; this cycle may be repeated until the volume of fluid pumped by the pump in order to reach the predetermined limit pressure (or liquid level) is lower than the threshold value; in this case, instead of opening the vent the communication with the user is opened (i.e. the first valve, or check valve of the infusion flow is opened) and the normal infusion procedure can recommence with the guarantee that all the excess air has been evacuated through the vent. In a second way, the pump is activated (with both valves closed), while the pressure increase (or the liquid level) is monitored downstream of the pump in relation to the volume of fluid displaced by the pump (this volume can be determined, for example, on the basis of the pump displacement, and in the specific case, in which the pump is rotary, on the basis of the number of revolutions made by the pump itself, or also, for example, on the basis of the weight measured by the weight sensor 3): if this ratio exceeds a certain threshold value, it means that in the fluid downstream of the pump there is a small quantity of gas in relation to liquid, so the normal infusion procedure can safely be restarted; on the other hand, if the above-mentioned ratio is lower than the threshold value after the pressure (or liquid level) downstream of the pump has reached a predetermined threshold value, the vent will be opened and the same operative cycle will be repeated. In a third way, the pump is activated (with both valves closed) up until it moves a predetermined volume of fluid, after which the pressure increase (or liquid level) is calculated downstream of the pump by effect of the displacement of the above-mentioned volume; if the increase in pressure (or liquid level) exceeds a certain threshold value, it means that the liquid part of the fluid downstream of the pump is relatively high in relation to the gas part, so that the infusion procedure can recommence in conditions of safety (therefore the block valve of the infusion flow is opened and the infusion fluid is pumped normally to the user); if the pressure increase (or liquid level) is lower than the above-mentioned threshold value, it means that downstream of the pump the gaseous part of the fluid present is relatively high in comparison with the liquid level, and the vent will therefore be opened to evacuate the excess gas before being newly closed, the operating cycle then being repeated. Other ways might be envisaged for performing the automatic degassing procedure, based on the monitoring of the pressure (or liquid level) downstream of he pump with one or another or both the two valves, the vent valve and the infusion block valve, in the closed position.

In a further way, an appropriate liquid level can be re-established without the use of the pressure sensor the liquid level sensor. In this further way the vent line 7 may be not ring-closed on the container 2 or on the infusion line 4, but may be connected in another way, for example to the line 21 or the atmosphere or to a drainage which is external of the infusion device. In this further way, after having filled the emptied container and after having replaced it with a full container of the infusion fluid (as in the preceding cases), the infusion pump may be activated with the vent valve open (the vent valve can be opened before, or during, or after the full container has replaced the emptied container). The controller in this case can be programmed to pump a predetermined quantity (in weight or volume) of infusion fluid, possibly mixed with air, or to pump at a predetermined velocity for a predetermined time. The quantity in weight can be detected by the weight sensor 3. The quantity in volume can be detected on the base of the capacity of the positive-displacement pump 5 and the number of operative cycles (rotations) of the pump. The controller is programmed to close the vent valve 8 and open the infusion block valve 6 after the pumping action has ensured appropriate filling of the separator (chamber 9) with liquid. The normal infusion procedure can recommence after a momentary pause of the infusion pump 5, but can restart even without having to stop the infusion pump 5.

LEGEND

1. Infusion apparatus
2. Batch container of the infusion fluid
3. Weight sensor
4. Infusion line
5. Infusion pump
6. First valve (check or block valve for the infusion fluid)
7. Vent line or excess gas discharge line
8. Second valve or vent valve
9. Infusion fluid expansion chamber (gas-liquid separation chamber)
10. First pressure sensor (pressure sensor downstream of the infusion pump)
11. Second pressure sensor (pressure sensor upstream of the infusion pump)
12. Vent line discharge (infusion line excess gas discharge)
13. Removable connection between the infusion line and the infusion fluid container
14. Blood treatment device having a semipermeable membrane (hemodialyser or hemo(dia)filter or plasma separator or hemoperfusion device or membrane exchanger)
15. Blood withdrawal line (arterial line)
16. Blood return line (venous line)
17. Blood pump
18. Source of a medical fluid (dialysis fluid source)
19. Fresh medical fluid supply line
20. Drainage
21. Used medical fluid discharge line
22. Removable connection between the vent line and the medical treatment apparatus
23. Extracorporeal blood circuit

The invention claimed is:
1. An infusion apparatus comprising:
at least a batch container containing an infusion fluid;
an infusion line having a first end which is connected to the batch container and a second end which is configured to supply the infusion fluid, the second end of the infusion line being directly connected to a blood withdrawal line or a blood return line;
an infusion pump operating on the infusion line and configured for circulation of the infusion fluid from the first end of the infusion line to the second end of the infusion line;
a first valve designed to open and close the infusion line between the pump and the second end;
a gas-liquid separator arranged in an intermediate tract of the infusion line extending between the infusion pump and the first valve;
a vent line having a first end which is connected to the gas-liquid separator and a second discharge end which is opposite the first end, the second discharge end of the vent line being directly connected to an element selected from the group of elements consisting of:
the batch container of the infusion fluid,
an initial tract of the infusion line comprised between the batch container and the infusion pump,
an aspiration device,
a fluid transport line connected to a fluid chamber of a blood treatment device having a semipermeable membrane which separates the fluid chamber from a blood chamber, and
a used fluid discharge line of a hemo(dia)filtration apparatus;
a second valve designed to open and close the vent line;
a first pressure sensor configured for emitting a first signal indicative of pressure in the intermediate tract;
a control unit programmed to:
close the first valve and the second valve,
activate the infusion pump,
receive the first signal,
determine at least one pressure change value based on the first signal,
compare the pressure change value with at least one reference value, and
open either the first valve or the second valve depending upon the outcome of the comparison.

2. The apparatus of claim 1, wherein the control unit is configured to open the first valve or the second valve according to whether the pressure change value is greater or, respectively, lower than the reference value.

3. The apparatus of claim 1, wherein the control unit is configured to determine the pressure change value in the intermediate tract during a predetermined change of another parameter while the pump is activated.

4. The apparatus of claim 3, wherein the another parameter is selected from the group of parameters consisting of the time, the volume/weight of fluid displaced by the pump, the displacement of a mobile element of the pump, and a weight of the batch container of the infusion fluid.

5. The apparatus of claim 3, wherein the pressure change value is placed in relation with or normalised with respect to said another parameter.

6. The apparatus of claim 1, wherein the gas-liquid separator comprises an expansion chamber.

7. The apparatus of claim 1, wherein the first end of the vent line is connected with or engaged to a top of the gas-liquid separator.

8. The apparatus of claim 1, wherein the first pressure sensor is associated to the gas-liquid separator.

9. The apparatus of claim 1, wherein the second end of the infusion line is connected to an extracorporeal blood circuit of an apparatus for extracorporeal blood treatment.

10. The apparatus of claim 1, comprising a weight sensor which emits a signal indicating a weight of the batch container, the control unit being programmed to perform the following stages: opening the first valve, closing the second valve, activating the pump with the first valve open and the second valve closed, acquiring at least a weight value of the batch container, comparing the weight value with a reference weight value, and signalling a faulty situation and/or stopping the pump and/or closing the first valve according to a result of the comparison.

11. The apparatus of claim 10, wherein the reference weight value comprises a previously acquired weight value of the batch container and wherein comparing comprises assessing whether the weight of the batch container is no longer decreasing, or wherein the reference weight value comprises a predefined value indicative of the weight of the empty fluid batch container.

12. The apparatus of claim 1, wherein the infusion pump is a volumetric pump.

13. The apparatus of claim 1, wherein the infusion pump is an occlusive pump.

14. The apparatus of claim 1, comprising a second pressure sensor for emitting a second signal indicating the pressure in an initial tract of the infusion line comprised between the batch container and the infusion pump.

15. The apparatus of claim 14, wherein the control unit is programmed to: acquire at least a pressure value in the initial tract supplied by the second pressure sensor, compare the pressure value in the initial tract with a reference value, and signal a faulty situation and/or stop the pump and/or close the first valve according to the comparison.

16. An infusion apparatus comprising:
an infusion line having a first end which is configured to be connected to a source of infusion fluid and a second end which is configured to supply the infusion fluid;
an infusion pump operating on the infusion line and configured for circulation of the infusion fluid from the first end to the second end;
a first valve designed to open and close the infusion line between the pump and the second end;
a gas-liquid separator arranged in an intermediate tract of the infusion line extending between the infusion pump and the first valve;
a vent line having a first end which is connected to the gas-liquid separator and a second end which is opposite the first end, the second end of the vent line being directly connected to an element selected from the group of elements consisting of:
the source of infusion fluid,
an initial tract of the infusion line comprised between the first end of the infusion line and the infusion pump,
an aspiration device,
a fluid transport line connected to a fluid chamber of a blood treatment device having a semipermeable membrane which separates the fluid chamber from a blood chamber, and
a used fluid discharge line of a hemo(dia)filtration apparatus;
a second valve designed to open and close the vent line;
a first pressure sensor configured for emitting a first signal indicative of pressure in the intermediate tract;
a control unit programmed to:
close the first valve and the second valve,
activate the pump while said first and second valves are closed, determine at least a value of pressure change in the intermediate tract taking place during a predetermined variation of another parameter while the pump is activated, compare the above-mentioned pressure change value with a reference value, and open either the first valve or the second valve according to the comparison.

17. The apparatus of claim 16 wherein the another parameter is selected from the group consisting of: the volume of fluid pumped by the infusion pump, a parameter indicative of this volume, the time, the displacement of a mobile element of the infusion pump, and the weight of a container of the infusion fluid.

18. An infusion apparatus comprising:

an infusion line having a first end which is configured to be connected to a source of infusion fluid and a second end which is configured to supply the infusion fluid;

an infusion pump operating on the infusion line and configured for circulation of the infusion fluid from the first end to the second end;

a first valve designed to open and close the infusion line between the pump and the second end;

a gas-liquid separator arranged in an intermediate tract of the infusion line extending between the infusion pump and the first valve;

a vent line having a first end which is connected to the gas-liquid separator and a second end which is opposite the first end;

a second valve designed to open and close the vent line;

a first pressure sensor configured for emitting a first signal indicative of pressure in the intermediate tract;

a second pressure sensor for emitting a second signal indicating the pressure in an initial tract of the infusion line comprised between the first end of the infusion line and the infusion pump;

a control unit programmed to:
close the first valve and the second valve,
activate the pump while said first and second valves are closed,
determine at least a value of pressure change in the intermediate tract taking place during a predetermined variation of another parameter while the pump is activated,
compare the above-mentioned pressure change value with a reference value, and
open either the first valve or the second valve according to the comparison.

19. An infusion apparatus comprising:

at least a batch container containing an infusion fluid;

an infusion line having a first end which is connected to the batch container and a second end which is configured to supply the infusion fluid, the second end of the infusion line being directly connected to a blood withdrawal line or a blood return line;

an infusion pump operating on the infusion line and configured for circulation of the infusion fluid from the first end of the infusion line to the second end of the infusion line;

a first valve designed to open and close the infusion line between the pump and the second end;

a gas-liquid separator arranged in an intermediate tract of the infusion line extending between the infusion pump and the first valve;

a vent line having a first end which is connected to the gas-liquid separator and a second discharge end which is opposite the first end;

a second valve designed to open and close the vent line;

a first pressure sensor configured for emitting a first signal indicative of pressure in the intermediate tract;

a second pressure sensor for emitting a second signal indicating the pressure in an initial tract of the infusion line comprised between the batch container and the infusion pump;

a control unit programmed to:
close the first valve and the second valve,
activate the infusion pump,
receive the first signal,
determine at least one pressure change value based on the first signal,
compare the pressure change value with at least one reference value, and
open either the first valve or the second valve depending upon the outcome of the comparison.

20. The apparatus of claim 19, wherein the control unit is configured to open the first valve or the second valve according to whether the pressure change value is greater or, respectively, lower than the reference value.

21. The apparatus of claim 19, wherein the control unit is configured to determine the pressure change value in the intermediate tract during a predetermined change of another parameter while the pump is activated.

22. The apparatus of claim 21, wherein the another parameter is selected from the group of parameters consisting of the time, the volume/weight of fluid displaced by the pump, the displacement of a mobile element of the pump, and a weight of the batch container of the infusion fluid.

23. The apparatus of claim 21, wherein the pressure change value is placed in relation with or normalised with respect to said another parameter.

24. The apparatus of claim 19, wherein the gas-liquid separator comprises an expansion chamber.

25. The apparatus of claim 19, wherein the first end of the vent line is connected with or engaged to a top of the gas-liquid separator.

26. The apparatus of claim 19, wherein the first pressure sensor is associated to the gas-liquid separator.

27. The apparatus of claim 19, wherein the second end of the infusion line is connected to an extracorporeal blood circuit of an apparatus for extracorporeal blood treatment.

28. The apparatus of claim 19, comprising a weight sensor which emits a signal indicating a weight of the batch container, the control unit being programmed to perform the following stages: opening the first valve, closing the second valve, activating the pump with the first valve open and the second valve closed, acquiring at least a weight value of the batch container, comparing the weight value with a reference weight value, and signalling a faulty situation and/or stopping the pump and/or closing the first valve according to a result of the comparison.

29. The apparatus of claim 28, wherein the reference weight value comprises a previously acquired weight value of the batch container and wherein comparing comprises assessing whether the weight of the batch container is no longer decreasing, or wherein the reference weight value comprises a predefined value indicative of the weight of the empty fluid batch container.

30. The apparatus of claim 19, wherein the infusion pump is a volumetric pump.

31. The apparatus of claim 19, wherein the infusion pump is an occlusive pump.

32. The apparatus of claim 19, wherein the control unit is programmed to: acquire at least a pressure value in the initial tract supplied by the second pressure sensor, compare the pressure value in the initial tract with a reference value, and signal a faulty situation and/or stop the pump and/or close the first valve according to the comparison.

* * * * *